(12) United States Patent
Saunois et al.

(10) Patent No.: US 10,493,303 B2
(45) Date of Patent: Dec. 3, 2019

(54) SOLID/LIQUID EXTRACTION

(75) Inventors: Alex Saunois, Nogent-le-Roi (FR); Jacques Legrand, Neuilly sur Eure (FR); Eglantine Mercier, Rambouillet (FR)

(73) Assignee: MINAFIN, Fonds Jean Paques (BE)

( * ) Notice: Subject to any disclaimer, the term of this patent is extended or adjusted under 35 U.S.C. 154(b) by 0 days.

(21) Appl. No.: 13/575,404

(22) PCT Filed: Jan. 31, 2011

(86) PCT No.: PCT/EP2011/051333
§ 371 (c)(1),
(2), (4) Date: Jul. 26, 2012

(87) PCT Pub. No.: WO2011/092334
PCT Pub. Date: Aug. 4, 2011

(65) Prior Publication Data
US 2012/0294887 A1 Nov. 22, 2012

(30) Foreign Application Priority Data

Jan. 29, 2010 (FR) ...................................... 10 50646
Jan. 28, 2011 (FR) ...................................... 11 50681

(51) Int. Cl.
| | | |
|---|---|---|
| *A61Q 19/00* | (2006.01) | |
| *A61K 8/92* | (2006.01) | |
| *A61K 8/97* | (2017.01) | |
| *C11B 1/10* | (2006.01) | |
| *C11C 1/02* | (2006.01) | |
| *C11C 3/00* | (2006.01) | |
| *A23L 33/10* | (2016.01) | |
| *A23L 33/105* | (2016.01) | |
| *A23L 33/115* | (2016.01) | |

(52) U.S. Cl.
CPC .............. *A61Q 19/00* (2013.01); *A23L 33/10* (2016.08); *A23L 33/105* (2016.08); *A23L 33/115* (2016.08); *A61K 8/922* (2013.01); *A61K 8/97* (2013.01); *C11B 1/10* (2013.01); *C11C 1/025* (2013.01); *C11C 3/003* (2013.01)

(58) Field of Classification Search
None
See application file for complete search history.

(56) References Cited

U.S. PATENT DOCUMENTS

| | | |
|---|---|---|
| 2,530,809 A | 11/1950 | Christensen et al. |
| 3,723,487 A | 3/1973 | Couche |
| 4,549,990 A | 10/1985 | Seguin et al. |
| 4,946,695 A * | 8/1990 | Forster ...................... C12C 3/10 426/286 |
| 5,262,163 A | 11/1993 | Rancurel |
| 5,403,514 A | 4/1995 | Matsuhisa et al. |
| 5,458,692 A | 10/1995 | Matsuhisa et al. |
| 6,146,616 A | 11/2000 | Msika et al. |
| 6,589,760 B1 | 7/2003 | Buchanan et al. |
| 6,673,952 B2 | 1/2004 | Lemaire et al. |
| 6,743,450 B2 | 6/2004 | Romanczyk et al. |
| 6,759,543 B2 | 7/2004 | Bardet et al. |
| 7,161,055 B2 | 1/2007 | Choo et al. |
| 2003/0017216 A1* | 1/2003 | Schmidt et al. .............. 424/725 |
| 2004/0018258 A1 | 1/2004 | Piccirilli et al. |
| 2005/0209468 A1 | 9/2005 | Burns |
| 2006/0086664 A1 | 4/2006 | Wills |
| 2006/0099323 A1* | 5/2006 | Piccirilli et al. .............. 426/655 |
| 2006/0287533 A1 | 12/2006 | Tatsuta |

(Continued)

FOREIGN PATENT DOCUMENTS

| | | |
|---|---|---|
| DE | 196 08 463 A1 | 9/1997 |
| DE | 10 2004 047 722 A1 | 4/2006 |

(Continued)

OTHER PUBLICATIONS

Matyash V, Liebisch G, Kurzchalia TV, Shevchenko A, Schwudke D. J Lipid Res. May 2008;49(5):1137-46.*
"Lipid Extraction using MTBE". Web Publication Date: Jul. 22, 2008 [Retrieved from the Internet on: Feb. 21, 2014]. Retrieved from: <URL: http://www.lipidomicnet.org/index.php/Lipid_extraction_using_MTBE>.*
Aul et al. "A Green alternative to THF". Manufacturing chemist (May 2007) 33-34.*
"Lipid Extraction". Internet Archive Date: Feb. 24, 2001 [Retrieved from the Internet on: May 18, 2015]. Retrieved from: <URL: https://web.archive.org/web/20010224063056/http://www.cyberlipid.org/extract/extr0001.htm>.*

(Continued)

*Primary Examiner* — Amy L Clark
(74) *Attorney, Agent, or Firm* — Potomac Law Group, PLLC

(57) ABSTRACT

The invention relates to a method for the solid/liquid extraction of an oil or butter, particularly having a high unsaponifiable content, contained in at least one solid vegetable matter or a micro-organism. The method includes at least the following steps: solid/liquid extraction of at least one solid vegetable matter or a micro-organism using a first solvent system comprising a concentration of solvent selected from among fluorinated aromatic solvents, particularly trifluorotoluene (BTF) and hexafluorobenzene (BHF), tert-butyl ethers, particularly 2-ethoxy-2-methylpropane, also known as ethyl-tert-butyl-ether (ETBE), and 2-methoxy-2-methylpropane or methyl-tert-butylether (MTBE), solvents comprising at least one silicon atom, particularly hexamethyldisiloxane (HMDS) and tetramethylsilane (TMS), methyltetrahydrofuran (MeTHF), and mixtures thereof, representing at least 50 vol.-% in relation to the total volume of the solvent system; and, optionally, recovery of a fraction comprising the oil or butter, particularly unsaponifiable enriched. The invention also relates to an unsaponifiable fraction, oil or butter obtained using this method and to compositions containing said oil or fraction.

11 Claims, No Drawings

(56) References Cited

U.S. PATENT DOCUMENTS

2008/0300386 A1    12/2008   Lazarev et al.
2009/0197839 A1     8/2009   Romero

FOREIGN PATENT DOCUMENTS

| | | | |
|---|---|---|---|
| EP | 1246633 B1 | 10/2002 | |
| FR | 2678632 A1 | 1/1993 | |
| FR | 2753200 A1 | 3/1998 | |
| FR | 2762512 | 10/1998 | |
| FR | 2762512 A1 | 10/1998 | |
| JP | 2002053474 A * | 2/2002 | |
| WO | WO 2008/017484 A1 | 2/2008 | |
| WO | WO-2008060571 A2 * | 5/2008 | C11B 1/10 |

OTHER PUBLICATIONS (U1) Reed et al. Br. phycol. J. 19 (Dec. 1, 1984) 381-383.*
(V1) Meir et al. J. Amer. Soc. Hort. Sci. 116(5):823-826. 1991.*
(W1) Hejazi et al. Biotechnology and Bioengineering. 79(1): 30-36. 2002.*
(X1) "Acros organics". Internet Pub Date: Jun. 2008 [Retrieved from the Internet on: Mar. 16, 2017]. Retrieved from: <URL: http://www.acros.com/portal/alias__rainbow/lang__en/tabID__151/DesktopDefault.aspx>.*
Comanita, B. "Methyltetrahydrofuran: simply better than tetrahydrofuran." Jun. 29, 2007 [Retrieved from the Internet on: Oct. 26, 2017]. Retrieved from: <URL: https://acs.confex.com/acs/green07/techprogram/P39950.HTM>. Abstract. (Year: 2007).*
International Search Report issued in application No. PCT/EP2011/051333 dated Dec. 13, 2011.
"Chemicals Known or Suspected to Cause Cancer or Reproductive Toxicity," California Department of Public Health Occupational Health Branch California Safe Cosmetics Program, Nov. 1, 2012, (Sep. 1, 2009 in specification), pp. 1-36.
"CMR le Cancerogene-Mutagene-toxique pour la Reproduction (The European regulatory classification regarding carcinogenic, mutagenic and reprotoxic chemicals)," CNRS—PRC, Apr. 31, 2009, www.prc.cnrs-gif.fr/en_telechargement/cmr31.pdfn, 1 page.
"Directives—Commission Directive 2009/2/EC of Jan. 15, 2009," Official Journal of the European Union, Jan. 16, 2009, http://eur-lex.europa.eu/LexUriServ/LexUriServ.do?uri=OJ:L:2009:011:0006:0082:FR:PDF, pp. L 11/6-L 11-82.
Hansen, "The Three Dimensional Solubility Parameter and Solvent Diffusion Coefficient," Chapters 1-8, pp. 1-106, Copenhagen, Danish Technical Press, 1967.
Gregory et al., "Who needs alternative solvents and criteria for their selection?," Technology and Solvents for Extracting Oilseeds and Nonpetroleum Oil, Wan et al., eds., AOCS Press, p. 1, 1997.
Fine et al., "Agro-solvents for the oilseed extraction," OCL, vol. 20, No. 5, A502, 2013.
"Standard for Solvent Extraction Plants," NFPA 36, 2001 Edition, pp. 36-1-36-2, 2001.

* cited by examiner

SOLID/LIQUID EXTRACTION

The present invention relates to a method for the solid/liquid extraction of an oil or butter from a solid vegetable matter or a micro-organism; in particular, said oil or said butter comprises a high unsaponifiable content.

Unsaponifiables or unsaponifiable fractions of a fat consist of compounds forming the portion of a fat which, after prolonged action of an alkaline base, remains insoluble in water and can be extracted with an organic solvent.

Most vegetable oil unsaponifiables include major categories of substances. These major categories include saturated or unsaturated hydrocarbons, aliphatic or terpene alcohols, sterols, tocopherols, carotenoid pigments, xanthophylls, and one or two specific categories in the case of some oils.

The usual methods for obtaining unsaponifiables from vegetable oils aim to extract all or part of the major categories contained therein, suitable for preparing partial or total unsaponifiable fractions.

Partial or total unsaponifiable fractions are particularly sought for the pharmacological, cosmetic and nutritional properties thereof.

The usual methods for obtaining unsaponifiables from vegetable oils include, among others, a fat saponification step and extraction of the target product (the unsaponifiable) with an organic solvent.

The solvents most commonly used for extracting oils, particularly those rich in unsaponifiables, from solid vegetable matter are aliphatic solvents, particularly hexane.

Hexane particularly involves the drawback of being reprotoxic; it is particularly classified as CMR Category 3 in EU1 CMR list or in EU2 CMR list.

Hexane has the further drawback of being hazardous to handle, namely due to the physicochemical properties thereof, particularly the flash point thereof (−23.3° C.) and/or the self-ignition temperature thereof (233.9° C.).

Finally, methods involving these conventional aliphatic solvents, particularly hexane, may be unsatisfactory in terms of yield, with respect to the oil and/or with respect to the unsaponifiable content of the oil obtained, selectivity, simplicity, cost, toxicity, convenience, number of steps, particularly extraction, and/or rapidity.

The aim of the present invention is therefore that of solving all or part of the problems mentioned above. In particular, the aim of the invention is that of providing a method that is more economical, more direct, more environmentally-friendly, requires a smaller quantity of organic solvent, is easier to implement, quicker, generates less toxic conditions, suitable for obtaining oils, particularly having a high unsaponifiable content, which is at least comparable, or superior, in terms of yield and/or selectivity, with respect to existing methods.

In particular, it is desirable for the solvent(s) involved to be less toxic, namely not classified as a CMR substance, namely an EU2 CMR list substance, and/or suitable for extracting oils with a yield and/or selectivity at least comparable to the yields and selectivities obtained using conventional aliphatic solvents, particularly hexane.

Solvents said to be "classified as a CMR substance" may be those included in the list in the annexes of the directive 2009/2/EC of 15 Jan. 2009, particularly available at the address http://eur-lex.europa.eu/LexUriServ/LexUriServ.do?uri=OJ:L:2009:011:0006:0082:FR:PDF, this first list hereinafter being referred to as "EU1 CMR list", those listed in the European Regulatory Classification of chemicals listed as carcinogenic, mutagenic and toxic for reproduction −31$^{st}$ ATP, 2009, particularly available at the address http://www.prc.cnrs-gif.fr/en_telechargement/cmr31.pdfn, this second list being hereinafter referred to as "EU2 CMR list", and/or those listed in the list of "Chemicals known or suspected to cause cancer or reproductive toxicity" dated 1 Sep. 2009 drafted by the "California department of public health, occupational health branch, California safe cosmetic program" associated with the "California Safe Cosmetics Act of 2005", this third list hereinafter being referred to as the "US CMR list".

The expression EU CMR list used herein is used to refer to EU1 CMR list and EU2 CMR list, particularly EU2 CMR list.

The present invention thus relates to a method for the solid/liquid extraction of an oil or butter, particularly having a high unsaponifiable content, contained in at least one solid vegetable matter or a micro-organism, including the following steps:

solid/liquid extraction of at least one solid vegetable matter or a micro-organism using a first solvent system comprising a concentration of solvent selected from among fluorinated aromatic solvents, particularly trifluorotoluene (BTF) and hexafluorobenzene (BHF), tert-butyl ethers, particularly 2-ethoxy-2-methylpropane, also known as ethyl-tert-butyl-ether (ETBE), and 2-methoxy-2-methylpropane or methyl-tert-butylether (MTBE), solvents comprising at least one silicon atom, particularly hexamethyl disiloxane (HMDS) and tetramethylsilane (TMS), methyl-tetrahydrofuran (MeTHF), and mixtures thereof, representing at least 50% by volume in relation to the total volume of the solvent system, optionally, recovery of a fraction comprising the oil or butter, particularly enriched with unsaponifiable.

The CAS number of these various solvents are as follows BTF: 98-08-8; BHF: 392-56-3; ETBE: 37-92-3; MTBE: 1634-04-4; HMDS: 107-46-0; TMS: 75-76-3; and MeTHF: 96-47-9.

The term "high unsaponifiable content" according to the present invention indicates that the oil or butter includes at least 1% by mass, namely at least 2% by mass, and particularly 3% by mass, of the unsaponifiable compounds initially present in the solid matter.

The first solvent system may include a concentration of solvent selected from among fluorinated aromatic solvents, particularly trifluorotoluene (BTF) and hexafluorobenzene (BHF), tort-butyl ethers, particularly 2-ethoxy-2-methylpropane, also known as ethyl-tert-butyl-ether (ETBE), and 2-methoxy-2-methylpropane or methyl-tert-butylether (MTBE), solvents comprising at least one silicon atom, particularly hexamethyl disiloxane (HMDS) and tetramethylsilane (TMS), methyl-tetrahydrofuran (MeTHF), and mixtures thereof, representing at least 60%, namely at least 75%, particularly at least 90%, more particularly at least 95%, even more particularly at least 99% by volume in relation to the total volume of the first solvent system.

In particular, the first solvent system consists of fluorinated aromatic solvent, particularly trifluorotoluene (BTF) and hexafluorobenzene (BHF), tert-butyl ether, particularly 2-ethoxy-2-methylpropane, also known as ethyl-tert-butyl-ether (ETBE), and 2-methoxy-2-methylpropane or methyl-tert-butylether (MTBE), solvent comprising at least one silicon atom, particularly hexamethyl disiloxane (HMDS) and tetramethylsilane (TMS), methyl-tetrahydrofuran (MeTHF), or a mixture thereof.

The first solvent system may include a concentration of a solvent selected from among fluorinated aromatic solvents, particularly trifluorotoluene (BTF) and hexafluorobenzene (BHF), tert-butyl ethers, particularly 2-ethoxy-2-methylpropane, also known as ethyl-tert-butyl-ether (ETBE), and 2-methoxy-2-methylpropane or methyl-tert-butylether (MTBE), solvents comprising at least one silicon atom, particularly hexamethyl disiloxane (HMDS) and tetramethylsilane (TMS), methyl-tetrahydrofuran (MeTHF), and mixtures thereof, representing at least 50%, namely at least 75%, particularly at least 900, more particularly at least 95%, even more particularly at least 99% by volume in relation to the total volume of the first solvent system.

According to one alternative embodiment, the first solvent system consists of a solvent selected from among fluorinated aromatic solvents, particularly trifluorotoluene (BTF) and hexafluorobenzene (BHF), tert-butyl ethers, particularly 2-ethoxy-2-methylpropane, also known as ethyl-tert-butyl-ether (ETBE), and 2-methoxy-2-methylpropane or methyl-tert-butylether (MTBE), solvents comprising at least one silicon atom, particularly hexamethyl disiloxane (HMDS) and tetramethylsilane (TMS), methyl-tetrahydrofuran (MeTHF).

The invention also relates to a method for obtaining a particularly total or partial unsaponifiable fraction, including the following steps:

solid/liquid extraction of at least one solid vegetable matter or a micro-organism using a first solvent system comprising a concentration of solvent selected from among fluorinated aromatic solvents, particularly trifluorotoluene (BTF) and hexafluorobenzene (BHF), tert-butyl ethers, particularly 2-ethoxy-2-methylpropane, also known as ethyl-tert-butyl-ether (ETBE) and 2-methoxy-2-methylpropane or methyl-tert-butylether (MTBE), solvents comprising at least one silicon atom, particularly hexamethyl disiloxane (HMDS) and tetramethylsilane (TMS), methyl-tetrahydrofuran (MeTHF), and mixtures thereof, representing at least 50% by volume in relation to the total volume of the solvent system, optionally, recovery of an organic solution enriched with oil or butter, or recovery of the oil or butter, in particularly said oil or butter is enriched with unsaponifiable, conversion of said oil or butter into hydroalcoholic solution, particularly by means of a step selected from among saponifications and esterifications, extraction of the hydroalcoholic solution wherein the fat fraction is separated from the unsaponifiable fraction by means of liquid/liquid extraction or distillation, and recovery of the particularly partial or total unsaponifiable fraction.

The term "total fraction" according to the present invention indicates that this fraction includes all the constituent categories of substances of the unsaponifiable contained in the vegetable oil or butter or in the micro-organism in question.

The term "partial fraction" according to the present invention indicates that this fraction includes at least one of the constituent categories of substances of the unsaponifiable contained in the vegetable oil or butter or in the micro-organism in question.

The first solvent system is as defined for the method for the solid/liquid extraction of the oil or butter.

Said oil or butter may be converted into hydroalcoholic solution in a conventional solvent system.

According to one particular alternative embodiment, said oil or butter is converted into hydroalcoholic solution in a second solvent system comprising, or consisting of, at least one solvent from the first solvent system, particularly methyltetrahydrofuran (MeTHF).

More particularly, the conversion may be carried out without total purification of the oil or butter. In particular, the conversion is carried out directly on the organic solution base enriched with oil or butter, particularly comprising at least 2% by mass, particularly at least 5% by mass, or at least 10% by mass of oil in relation to the total mass of the organic solution enriched with oil or butter.

According to a first alternative embodiment, the conversion is carried out on a particularly partially evaporated fraction, to which at least 50% by mass of other solvents is added, or no other solvents are added.

According to a further alternative embodiment, at least 10% of at least one other solvent, such as C2 to C4 alcohols, particularly ethanol, n-propanol, iso-propanol, butanol, particularly n-butanol, methyltetrahydrofuran (MeTHF) and mixtures thereof, may be added to the particularly evaporated organic solution enriched with oil.

Advantageously, the first and second solvent systems comprise methyltetrahydrofuran (MeTHF). In this case, the method may have the advantage of being enhanced in relation to conventional methods, for example in terms of yields, toxicity (non-CMR solvent) and selectivity.

If the hydroalcoholic solution is extracted using a liquid/liquid extraction, this may be performed with a third solvent system defined in the same way as the first solvent system, particularly with some of the same solvents as those used in the first and/or second solvent system.

In the latter case, the method is advantageous in economic terms and/or in terms of time in that it particularly involves easier solvent procurement and/or quality control management.

As a general rule, the method may be more economical, more direct, more environmentally-friendly as it requires a smaller quantity of organic solvent, easier to implement, quicker, generate less toxic conditions, suitable for obtaining oils, particularly having a high unsaponifiable content, and at least comparable, or superior, in terms of yield and/or selectivity, with respect to existing methods.

The saponification and extraction part may particularly be carried out according to the procedures described in FR 1 246 633.

The solid vegetable matter or the micro-organism used in the present methods may be obtained from soybean, rapeseed, corn, sunflower, sesame, lupin, cotton, coconut, olive, avocado, cocoa, illipe, shea, palm kernel, peanut, copra, linseed, castor, grape seeds, gourd seeds, blackcurrant seeds, melon seeds, tomato seeds, pumpkin seeds, almond, hazelnut, walnut, evening primrose, borage, safflower, camelina, poppy seed, macroalgae, microalgae, such as *Haematococcus, Dunaliella, Spirulina, Chorella*, and/or micro-organisms, particularly from marine, freshwater or terrestrial sources, particularly yeasts, moulds and more particularly bacteria and mixtures thereof.

Typically, the unsaponifiable fraction contents obtained range from 2 to 10% in avocado oil, are approximately 0.5% in coconut oil, approximately 1% in soybean oil and approximately 1% in olive oil.

Those skilled in the art would know the methods to be implemented to extract the unsaponifiable fraction from a vegetable oil or butter or a micro-organism and would know how to apply same to the conversion, extraction and/or recovery part of the unsaponifiable according to the present invention.

The prior art relating to this part particularly includes the method for preparing avocado oil unsaponifiable as described and claimed in the patent FR 2 678 632 held by Laboratoires Pharmascience. This method is suitable for obtaining an avocado oil unsaponifiable rich in furan fraction, also referred to as fraction H, compared to conventional methods for preparing avocado oil unsaponifiable.

In this way, the avocado oil unsaponifiable may be prepared from the previously heat-treated fruit, prior to the oil extraction and saponification, as described in the patent FR 2 678 632.

This heat treatment consists of controlled drying of the fruit, which is preferably fresh, for at least four hours, advantageously at least 10 hours, preferably between approximately 24 and approximately 48 hours, at a temperature preferably of at least approximately 80° C. and preferably between approximately 80 and approximately 120° C.

The method for preparing soybean oil unsaponifiable, obtained from a soybean oil unsaponifiable concentrate, may also be cited.

Said unsaponifiable concentrate may be prepared by means of molecular distillation according to a method as described for lupin oil in the patent application FR 2 762 512, but suitable for soybean oil.

In this method, the soybean oil is distilled in a centrifugal or scraped film molecular distiller, at a temperature between approximately 210 and 250° C. and subject to a high vacuum, between 0.01 and 0.001 millimetres of mercury (i.e. 0.13 to 1.3 Pa).

The distillate obtained has an unsaponifiable content between 5 and 40% by mass and thus is a soybean oil unsaponifiable concentrate.

The concentrate is then saponified with a base such as potash or sodium hydroxide in a polar medium, particularly an alcoholic medium, preferably ethanol, n-propanol, iso-propanol, butanol, particularly n-butanol, methyl-tetrahydrofuran (MeTHF), or a mixture thereof, and is then subjected to one or a plurality of extractions using the first solvent system.

The extraction solution obtained is preferably then centrifuged, filtered and washed with water to remove any traces of alkalinity.

The extraction solvent is carefully evaporated to recover the unsaponifiable. Finally, before the saponification thereof, the oil or butter may be previously enriched with unsaponifiable by separating a majority of the constituents of the unsaponifiable recovered in a concentrate. Various methods may be used: cold crystallisation, liquid/liquid extraction, or molecular distillation.

Prior unsaponifiable concentration of the oil or butter makes it possible to reduce the volumes of oil or butter to be saponified.

Molecular distillation is particularly preferred, preferably carried out at a temperature between approximately 180 and approximately 230° C. maintaining a pressure between $10^{-3}$ and $10^{-2}$ mm Hg and preferably in the region of $10^{-3}$ mm Hg.

The unsaponifiable concentration of the distillation may be up to 60% by mass in relation to the total mass.

Most particularly, the present invention relates to a method as described in the present description wherein the unsaponifiable obtained is selected from among a soybean unsaponifiable, an avocado unsaponifiable, particularly an avocado unsaponifiable enriched with furan fraction and/or an avocado unsaponifiable enriched with sterol fraction, and more particularly a mixture of avocado and soybean unsaponifiables (ASU).

The term "unsaponifiable enriched with X fraction" according to the present invention indicates that the X fraction content in the unsaponifiable is increased, particularly by at least 10% by mass, namely at least 50% by mass, more particularly at least 80% by mass.

The present invention also relates to an oil or butter devoid of solvents classified in EU1 CMR list, EU2 CMR list and/or the US CMR list, in particular said oil or butter is obtained using the method according to the present invention.

The present invention also relates to a particularly partial or total unsaponifiable fraction, devoid of solvents classified in EU1 CMR list, EU2 CMR list and/or the US CMR list, in particular said fraction is obtained using the extraction method according to the present invention.

The present invention also relates to the use of this fraction of said butter or oil for preparing a composition, particularly a pharmaceutical, nutritional and/or cosmetic composition, or a nutritional supplement.

The present invention also relates to a composition, particularly a pharmaceutical, nutritional or cosmetic composition, or a nutritional supplement, comprising at least one oil, butter or unsaponifiable fraction of at least one vegetable oil or butter or a micro-organism, said oil, butter or fraction being devoid of solvents classified in EU1 CMR list, EU2 CMR list and/or the US CMR list and/or said oil, butter or fraction is suitable for being obtained, or obtained directly, using the method according to the invention, and said composition optionally comprising an excipient, particularly a cosmetically, nutritionally or pharmaceutically acceptable excipient.

According to one particular embodiment, the present invention relates to a composition, particularly a pharmaceutical, nutritional and/or cosmetic composition, or a nutritional supplement, comprising at least one unsaponifiable, particularly a soybean unsaponifiable, an avocado unsaponifiable, more particularly an avocado unsaponifiable rich in furan fraction and/or an avocado unsaponifiable rich in sterol fraction, and even more particularly a mixture of avocado and soybean unsaponifiables (ASU) suitable for being obtained or obtained directly using the method according to the invention.

The pharmaceutical compositions may be intended for the prevention and/or treatment of connective tissue disorders, particularly arthrosis, periodontal disease and/or skin ageing.

The nutritional compositions, or nutritional supplements, may be intended for the prevention and/or treatment of connective tissue disorders, particularly arthrosis, periodontal disease and/or skin ageing and/or skin inflammation.

The cosmetic compositions may be intended for the prevention and/or treatment of epidermal, dermal and/or hypodermal skin disorders.

The term "devoid of solvents classified in EU1 CMR list, EU2 CMR list and/or the US CMR list" according to the present invention indicates a total content of solvents classified in EU1 CMR list, EU2 CMR list and/or the US CMR list less than 10 ppm, namely less than 5 ppm, particularly less than 2 ppm, or less than 1 ppm.

The present invention also relates to a cosmetic treatment method such that the cosmetic composition according to the invention is applied topically and also the use of an oil, butter, or unsaponifiable of a vegetable oil or butter or a micro-organism obtained according to the present invention for the manufacture of a medicinal product, particularly intended for treating and preventing connective tissue disorders, namely arthrosis.

Obviously, the various features described in the present description may be combined together.

As examples illustrating the present invention, the following experiments were conducted.

EXAMPLES

In all the examples, a reference test using hexane was carried out.

Example 1: Extraction from Dried Avocados

Extraction from dried avocados was carried out with hexane (reference) and with the following solvents: HMDS, MeTHF, BTF, BHF, MTBE, ETBE.

Dried avocado is ground and introduced into a cellulose cartridge (30 to 40 g). The extraction is carried out in a Soxhlet type device (BUCHI B-811). Four extractions are then launched in parallel and each consists of 20 extraction/siphoning cycles. Once the extraction has been finalised, the extraction solvent is evaporated and the residue from which solvent has been removed is weighed. The mass yields are then compared. The results are given in table 1.

TABLE 1

| Extraction solvent | Oil yield (% m/m) | Unsaponifiable oil content (% m/m) |
|---|---|---|
| Hexane | 61.1 | 1.88 |
| ETBE | 59.7 | 2.75 |
| MeTHF | 61.3 | 3.05 |
| HFB | 59.3 | 2.32 |
| BTF | 64.0 | 2.41 |
| HMDS | 60.5 | 1.92 |
| MTBE | 65.3 | 1.92 |

This demonstrates that the solvents according to the invention have an equivalent extraction capacity to that of hexane.

The unsaponifiable content of the extracted oil is higher for the solvents according to the invention than for hexane; it is increased by 50% in the case of ETBE and MeTHF.

Example 2: Extraction from Freeze-Dried Avocado Pulp Powder

Freeze-dried avocado pulp powder was extracted according to the method described in example 1 with hexane (reference) and with the following solvents: HMDS, MeTHF, BTF, MTBE, ETBE. The results are given in table 2.

TABLE 2

| Extraction solvent | Oil yield (% m/m) | Unsaponifiable oil content (% m/m) |
|---|---|---|
| Hexane | 70.1 | 2.15 |
| ETBE | 69.6 | 2.25 |
| MeTHF | 71.7 | 3.02 |
| BTF | 67.3 | 2.22 |
| HMDS | 68.8 | 2.22 |
| MTBE | 70.1 | 2.35 |

This demonstrates that the solvents according to the invention have an equivalent extraction capacity to that of hexane.

The unsaponifiable content of the extracted oil is higher for the solvents according to the invention than for hexane; it is increased by 50% in the case of 50% in the case of MeTHF.

Example 3: Oil Extraction from Dried Avocados

Extraction from dried avocados is carried out with hexane (reference) and the following solvents: BTF and ETBE.

Dried avocado is ground and introduced into a cellulose cartridge (30 to 40 g). The extraction is carried out in a Soxhlet type device (BUCHI B-811). Four extractions are then launched in parallel, the first consisting of 5 extraction cycles, the second of cycles, the third of 15 cycles and the fourth of 20 cycles. Once the extraction has been finalised, the extraction solvent is evaporated and the residue from which solvent has been removed is weighed. The mass yields are then compared.

The results are given in table 3 below.

TABLE 3

| | Solvent | | | | | | | | |
|---|---|---|---|---|---|---|---|---|---|
| | Hexane | | | | ETBE | | | | BTF |
| Cycles | 5 | 10 | 15 | 20 | 5 | 10 | 15 | 20 | 5 |
| Oil yield (% m/m) | 18.3% | 31.3% | 33.1% | 40.9% | 17.6% | 26.8% | 30.2% | 40.3% | 39.0% |

The mass yields obtained with ETBE are similar to those obtained with the hexane reference: ETBE thus offers an alternative to the use of hexane in solid/liquid extraction methods.

The extraction power of BTF is suitable for obtaining, in only 5 extraction cycles, the same yield as those obtained in 20 extraction cycles with hexane or ETBE. BTF thus offers a satisfactory alternative to the use of hexane suitable for reducing the quantity of solvent and/or contact time involved significantly.

Example 4: Extraction from Dried Chorella

Extraction from dried *Chorella* powder was carried out according to the method described in example 1 with hexane (reference) and with the following solvents: BTF and MTBE. The results are given in table 4.

TABLE 4

| Extraction solvent | Oil yield (% m/m) | Unsaponifiable oil content (% m/m) |
|---|---|---|
| Hexane | 70 | 3.0 |
| MTBE | 65.4 | 3.7 |
| BTF | 72 | 3.4 |

This demonstrates that the solvents according to the invention have an equivalent extraction capacity to that of hexane.

The unsaponifiable content of the extracted oil is higher for the solvents according to the invention than for hexane.

The invention claimed is:

1. A method for extracting an oil or butter, contained in at least one solid vegetable matter or an algae, comprising the following steps:
    solid/liquid extraction of a) an algae or b) at least one solid wherein said solid is obtained from soybean, rapeseed, corn, sunflower, sesame, lupin, cotton, coconut, olive, avocado, cocoa, illipe, shea, palm kernel, peanut, copra, linseed, castor, grape seeds, gourd seeds, blackcurrant seeds, melon seeds, tomato seeds, pumpkin seeds, almond, hazelnut, walnut, evening primrose, borage, safflower, camelina, or poppy seed, using a first solvent system comprising at least 50% by volume, in relation to the total volume of said solvent system, of a solvent selected from the group consisting of ethyl-tert-butyl-ether (ETBE), methyl-tetrahydrofuran (MeTHF), hexafluorobenzene (BHF), tetramethylsilane (TMS), and mixtures thereof, and
    recovery of a fraction from the solid-liquid extraction, wherein the fraction comprises the oil or butter, wherein said oil or butter comprises at least 1% by mass of unsaponifiable compounds present in the solid vegetable matter or algae.

2. The method according to claim 1, further comprising the following steps:
    conversion by saponification or esterification of said oil or butter in the recovered fraction into a hydroalcoholic solution,
    extraction of the hydroalcoholic solution wherein a fat fraction is separated from an unsaponifiable fraction by liquid/liquid extraction.

3. The method according to claim 1, wherein the first solvent system includes a concentration of solvent selected from the group consisting of ethyl-tert-butyl-ether (ETBE), methyl-tetrahydrofuran (MeTHF), hexafluorobenzene (BHF), tetramethylsilane (TMS), and mixtures thereof, of at least 75%, by volume in relation to the total volume of the first solvent system.

4. The method according to claim 1, wherein the first solvent system includes a concentration of a solvent selected from the group consisting of ethyl-tert-butyl-ether (ETBE), methyl-tetrahydrofuran (MeTHF), hexafluorobenzene (BHF), tetramethylsilane (TMS), and mixtures thereof, of at least 90%, by volume in relation to the total volume of the first solvent system.

5. The method according to claim 2, wherein said oil is converted into a hydroalcoholic solution with a second solvent comprising at least one solvent from the first solvent system.

6. The method according to claim 5, wherein the first and second solvent systems comprise methyltetrahydrofuran (MeTHF).

7. The method according to claim 5, wherein the extraction of the hydroalcoholic solution is performed by liquid/liquid extraction with a third solvent system comprising at least one solvent from the first and/or second solvent system.

8. The method according to claim 1, wherein the unsaponifiable compounds are a soybean unsaponifiable, avocado unsaponifiables, avocado unsaponifiables enriched with furan fraction and/or avocado unsaponifiables enriched with sterol fraction, or a mixture of avocado and soybean unsaponifiables (ASU).

9. The method according to claim 1, wherein said oil or butter comprises at least 2% by mass of unsaponifiable compounds present in the solid vegetable matter or algae.

10. The method according to claim 1, wherein the algae is macroalgae or microalgae.

11. The method according to claim 10, wherein the algae is *Haematocococcus, Dunaliella, Spirulina*, or *Chorella*.

* * * * *